(12) United States Patent
Johansson et al.

(10) Patent No.: US 11,714,387 B2
(45) Date of Patent: Aug. 1, 2023

(54) METHOD FOR OPTIMIZATION OF A BIOPROCESSING SYSTEM

(71) Applicant: Cytiva Sweden AB, Uppsala (SE)

(72) Inventors: Mikael Johansson, Uppsala (SE); Pasi Juntikka, Uppsala (SE); Peter Toreheim, Uppsala (SE); Shivakumar Selvaraj, Bengaluru Karnataka (IN)

(73) Assignee: Cytiva Sweden AB, Uppsala (SE)

( * ) Notice: Subject to any disclaimer, the term of this patent is extended or adjusted under 35 U.S.C. 154(b) by 0 days.

(21) Appl. No.: 17/268,490

(22) PCT Filed: Aug. 30, 2019

(86) PCT No.: PCT/EP2019/073281
§ 371 (c)(1),
(2) Date: Feb. 15, 2021

(87) PCT Pub. No.: WO2020/043913
PCT Pub. Date: Mar. 5, 2020

(65) Prior Publication Data
US 2021/0263482 A1 Aug. 26, 2021

(30) Foreign Application Priority Data
Aug. 31, 2018 (GB) ..................................... 1814233

(51) Int. Cl.
*G05B 13/02* (2006.01)
(52) U.S. Cl.
CPC ................................ *G05B 13/0205* (2013.01)
(58) Field of Classification Search
CPC ........................... G05B 13/0205; C12M 41/48
See application file for complete search history.

(56) References Cited

U.S. PATENT DOCUMENTS

| 2007/0118431 A1* | 5/2007 | Johansson .......... G06Q 30/0621 705/26.5 |
| 2008/0109200 A1* | 5/2008 | Bartee ....................... C12P 7/06 703/12 |

(Continued)

FOREIGN PATENT DOCUMENTS

| WO | 2013/028828 A1 | 8/2012 |
| WO | 2018/122196 A1 | 7/2018 |

OTHER PUBLICATIONS

PCT International Search Report and Written Opinion for PCT/EP2019/073281 dated Nov. 14, 2019 (10 pages).

(Continued)

*Primary Examiner* — Kenneth M Lo
*Assistant Examiner* — Mohammed Shafayet
(74) *Attorney, Agent, or Firm* — Eversheds Sutherland (US) LLP

(57) ABSTRACT

The present invention relates to a computer implemented method (600) for optimization of a bioprocessing system (100) formed by interconnected or interconnectable bioprocessing units and configured to provide a desired system functionality, the method comprising obtaining (610) requirement data of a bioprocess, the requirement data being at least indicative of the desired system functionality, and indicative of a desired substance resulting from the operation of the bioprocess system, obtaining (620) unit data indicative of characteristics of a plurality of bioprocessing units, generating (630) at least one optimized or suitable bioprocessing system configuration capable to provide the desired system functionality, the bioprocessing system configuration comprising a selection of bioprocessing units from the plurality of bioprocessing units selected using the requirement data, the unit data and an objective function (Continued)

dependent on the requirement data and the unit data. The invention extends to a configuration system (500).

15 Claims, 11 Drawing Sheets

(56) References Cited

U.S. PATENT DOCUMENTS

| | | | | |
|---|---|---|---|---|
| 2012/0308988 | A1* | 12/2012 | Discenzo | C12M 41/36 |
| | | | | 435/3 |
| 2013/0218352 | A1* | 8/2013 | Iovanni | G05D 7/0617 |
| | | | | 700/282 |
| 2014/0358831 | A1* | 12/2014 | Adams | G06N 20/00 |
| | | | | 706/20 |
| 2019/0336886 | A1* | 11/2019 | Hyckenberg | C12M 33/00 |
| 2020/0065712 | A1* | 2/2020 | Wang | G06N 20/00 |

OTHER PUBLICATIONS

Great Britain Search Report for GB Application No. 1814233.1 dated Feb. 20, 2019 (4 pages).

Lienqueo et al., "Use of Expert Systems for the Synthesis of Downstream Protein Processes," Computers and Chemical Engineering, 2000, 24:2339-2350.

\* cited by examiner

METHOD FOR OPTIMIZATION OF A BIOPROCESSING SYSTEM

CROSS REFERENCE TO RELATED APPLICATIONS

This application claims the priority benefit of PCT/EP2019/073281, filed on Aug. 30, 2019, which claims the benefit of Great Britain Application No. 1814233.1, filed on Aug. 31, 2018, the entire contents of which are incorporated by reference herein.

TECHNICAL FIELD

The present invention relates to a method for optimizing a bioprocessing system. The invention further relates to a computer or a configuration system for performing the method.

BACKGROUND

A bioprocessing system is generally used to provide a particular system functionality, e.g. a bioprocessing system may be used to produce and/or separate a desired biological target substance. Thus, bioprocessing systems can be understood essentially as performing a train of process operations having inputs and delivering a biological output. Often these process operations are divided and performed by bioprocessing units, the units often being discrete components in a process flow.

Chromatography techniques can be used in a laboratory setting to provide a bioprocessing system capable of being adapted for different uses providing multiple system functionality, and thereby, multiple desired substances resulting from the operation of that bioprocess system, or on a larger scale for a dedicated bioprocessing system with a single desired system functionality, and a single desired substance resulting from the operation of the bioprocess system, for example a desired monoclonal antibody.

Other bioprocessing systems include large bioreactors and associated equipment, smaller scale bioreactors, for example as used in cellular and genetic therapies, and biological filtration systems. All of those will have at least one desired system functionality, and at least one desired substance resulting from the operation of the bioprocess system.

Dependent on the requirements of the bioprocess, a suitable bioprocessing system configuration must be defined or identified. This typically involves to identify a plurality of bioprocessing units and/or to identify how the identified plurality of bioprocessing units should be interconnected.

A problem with conventional solutions is that there is a vast selection of bioprocessing systems, and combinations of bioprocessing units, that are capable of providing the desired bioprocessing system functionality. To identify a suitable bioprocessing system from the vast selection of bioprocessing systems is time consuming and cumbersome.

A further problem is that sometimes only a partial bioprocessing system needs to be defined. I.e. an existing partial selection of bioprocessing units have been made, and need to be complemented with additional bioprocessing units to provide the particular system functionality. In one example, a partial chromatography bioprocessing system exists, and only needs to be complemented with additional bioprocessing units, such as a set of columns.

Additionally, a further problem exists in that, even if a suitable bioprocessing system, or additional bioprocessing units to complement an existing bioprocessing system, is identified, there is still a need to determine a suitable supply of associated consumable items, utility supply, suitable accessories, spares and maintenance schedules, and compatibility with such existing bioprocessing systems.

Thus, there is a need for a method for configuring a bioprocessing system, which, in certain embodiments addresses the problems mentioned above.

U.S. Pat. Nos. 6,785,805, and 7,725,356 are examples of online configurator tools which can be used to select test, measurement or automation equipment based on specifications and size, but they still lack, for example a means to select based on criteria such as a desired substance resulting from the operation of the bioprocessing system concerned.

Objects of the Invention

An objective of embodiments of the present invention is to provide a solution which mitigates or solves the drawbacks and problems described above.

SUMMARY OF THE INVENTION

The above and further objectives problems are achieved addressed by the subject matter described herein. Further advantageous implementation forms of the invention are further defined herein.

Herein, a bioprocessing system is a selected number of bioprocessing units, which together perform a desired system function, with a desired result, for example the production of a molecule, a macromolecule such as a protein, for example an antibody, separation, filtering, cell production, cell modification, or a combination of the above. Embodiments of the invention provide a method or configuration system which can recommend an optimised or suitable combination of bioprocessing units into a bioprocessing system, in a manner described below, for example optimized for attaining the desired functionality and substance output. As an example, the method or configuration system can provide recommendations of units needed for a capture step in chromatography column, as such the separation column, hold and buffer reservoirs needed and additionally a recommendation of the necessary consumables such as single use components like bags, tubing etc., as well as utility supply such as chromatography resin, and buffer liquids. The method can be performed at any location, for example at the bioprocessing system location, using a computer already designated for controlling an existing bioprocessing system (the 'EDGE'), at a third party hosted computer (the 'CLOUD'), or under the control of the vendor of the bioprocessing units behind a closed/secure gateway. The latter maintains the confidentiality of the data used to make the recommendations, and thereby allows more data to be considered, for example price data, and availability data, service and maintenance contract data.

According to a first aspect of the invention, the above mentioned and other objectives are achieved by a method for optimization of a bioprocessing system formed by interconnected or interconnectable bioprocessing units and configured to provide a desired system functionality, the method comprising obtaining requirement data of a bioprocess, the requirement data being at least indicative of the desired system functionality, and indicative of a desired substance resulting from the operation and/or the desired system functionality of the bioprocess system, obtaining unit data indicative of characteristics of a plurality of bioprocessing units, generating at least one optimized or suitable bioprocessing system configuration capable to provide the desired system functionality, the bioprocessing system configuration comprising a selection of bioprocessing units from the plurality of bioprocessing units selected using the requirement data, the unit data and an objective function dependent on the requirement data and the unit data.

In an embodiment according to the first aspect, the step of generating bioprocessing system configurations comprises identifying one or more candidate system configurations using the requirement data and the unit data, wherein a system configuration is identified if the unit data match the requirement data, an selecting the at least one optimized or suitable bioprocessing system configuration by optimizing a value of an objective function dependent on the requirement data and the unit data.

In an embodiment according to the first aspect, a plurality of optimized or suitable bioprocessing system configuration are selected by optimizing a plurality of values of the objective function dependent on the requirement data and where the selected bioprocessing system configurations are ranked using the plurality of values of the objective function.

In an embodiment according to the first aspect, obtaining unit data comprises compiling or reading records in a database, accessible by the computer, the unit data including specification data relating to each bioprocessing unit.

In an embodiment according to the first aspect, obtaining requirement data comprises receiving input of requirement data from a user.

In an embodiment according to the first aspect, the optimized or suitable bioprocessing system configuration further comprises information indicative of on how the selection of bioprocessing units are interconnected or interconnectable to each other.

An advantage of the embodiment according to the first aspect is that an improved selection of bioprocessing units can be performed. A further advantage is that selection of bioprocessing units can be in less complex manner. A further advantage is that selection of bioprocessing units can be performed faster.

According to a second aspect of the invention, the above mentioned and other objectives are achieved by a computer for optimization of a bioprocessing system formed by interconnected or interconnectable bioprocessing units and configured to provide a desired system functionality.

The advantages according to the second aspect are the same as for the first aspect.

Further applications and advantages of embodiments of the invention will be apparent from the following detailed description.

Figure 1:
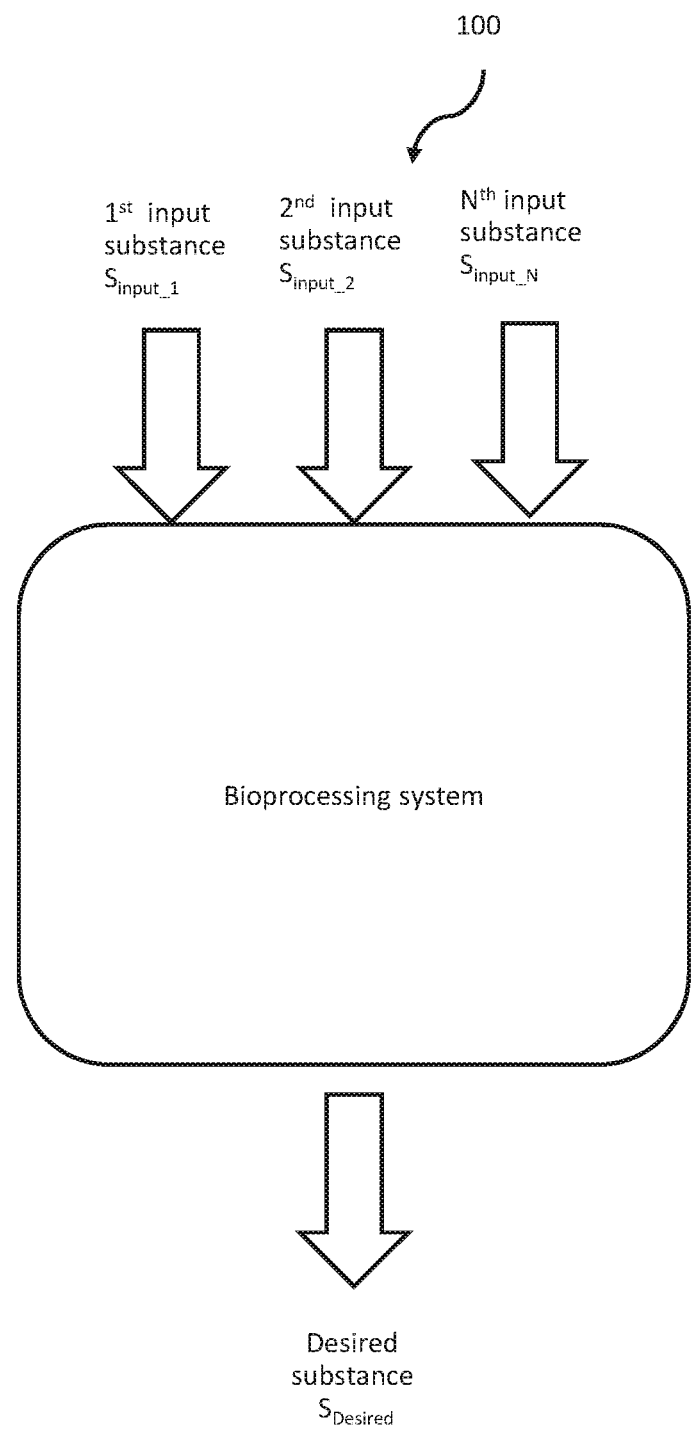
FIG. 1 shows a bioprocessing system according to one or more embodiments of the present disclosure.

A more complete understanding of embodiments of the invention will be afforded to those skilled in the art, as well as a realization of additional advantages thereof, by a consideration of the following detailed description of one or more embodiments. It should be appreciated that like reference numerals are used to identify like elements illustrated in one or more of the figures.

DETAILED DESCRIPTION

An "or" in this description and the corresponding claims is to be understood as a mathematical OR which covers "and" and "or", and is not to be understand as an XOR (exclusive OR). The indefinite article "a" in this disclosure and claims is not limited to "one" and can also be understood as "one or more", i.e., plural.

In the context of this disclosure, the term bioprocessing system may represent a complete bioprocess workflow involving multiple process steps and unit operations or alternatively the term may represent one or more individual process steps or unit operations and/or bioprocessing units. One schematic example of a complete bioprocess workflow involving multiple process steps ad unit operation is disclosed in FIG. 11.

Figure 11:
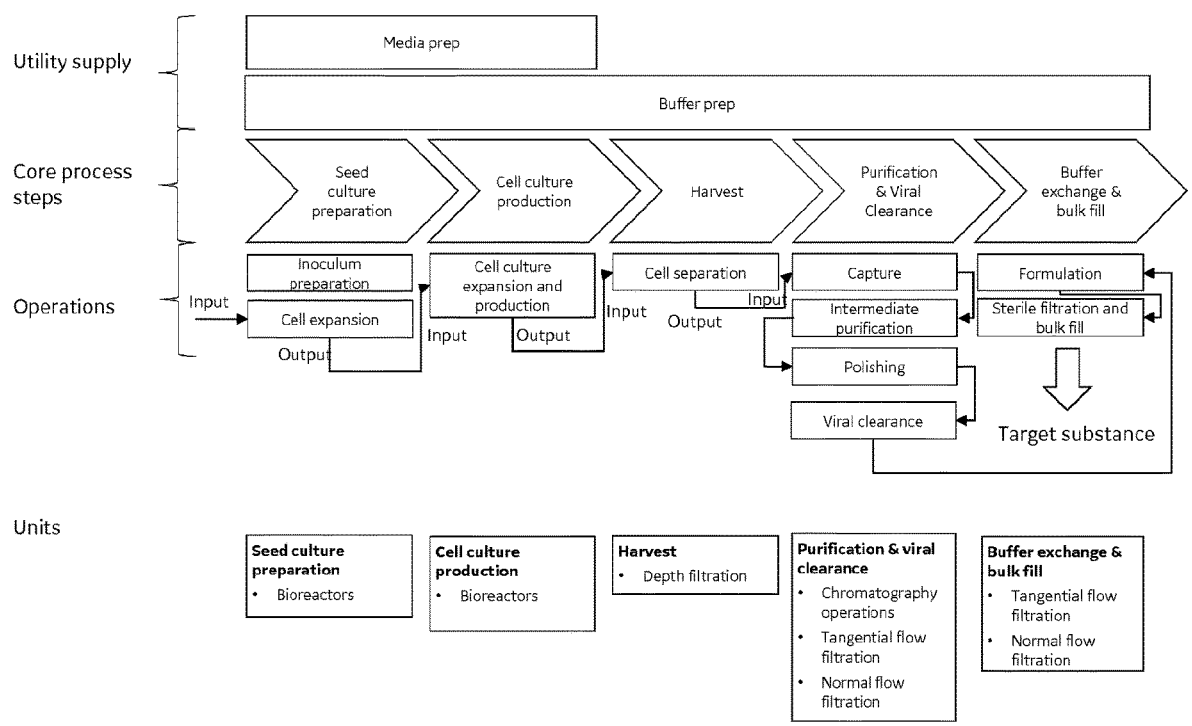
FIG. 11 is a schematic example of a complete bioprocess workflow involving multiple process steps and unit operation.

In FIG. 11, the top level represents the utility supplies like cell culture media and process buffers or the like. The second level from the top represents the core process steps:
Seed culture preparation
Cell culture production
Harvest
Purification and viral clearance
Buffer exchange and bulk fill The third level represents examples of the individual process operations for each one of the core process steps. And the fourth level represents key system units used in each one of the core process steps. In the disclosed example the core process step of seed culture preparation involves the use of one or more smaller bioreactors for expanding the cell culture from e.g. a frozen vial of cells from a cell bank to a cell culture of sufficient volume and density that can be used to set up the final cell culture in the production bioreactor, the size of which is selected based on the desired process outcome and it may e.g. be 500 liters or larger. The production bioreactor may be operated in any suitable mode of operation, such as fed-batch, perfusion or the like. The harvest step may e.g. be performed using a depth filtration unit, but other units may be used as is disclosed in more detail below.

The purification and viral clearance process step may be comprised of several sub steps depending on the target substance to be purified. In the example of FIG. 11, it comprises capture, intermediate purification, polishing and viral clearance steps and the corresponding process units may comprise one or more chromatography system, tangential flow filtration and normal flow filtration.

As is evident from FIG. 11 the selection of units and optimization of a complete bioprocess system or subsections thereof is a very complex and difficult task.

Figure 10:
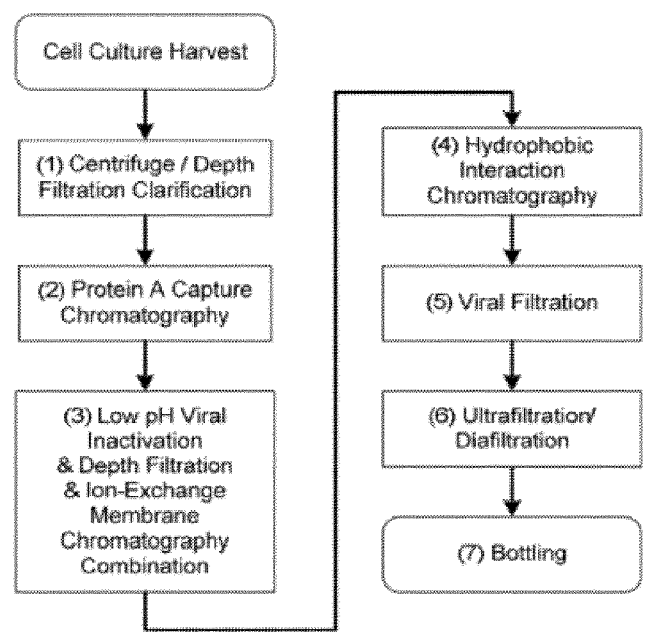
FIG. 10 schematically shows an example of a purification process for purifying a monoclonal antibody from a cell culture harvest.

FIG. 10 schematically shows an example of a purification process for purifying a monoclonal antibody from a cell culture harvest involving multiple chromatography steps in order to meet purity, yield, and throughput requirements. The steps typically involve capture, intermediate purification or polishing, and final polishing. Affinity chromatography (Protein A or G) or ion exchange chromatography is often used as a capture step. Traditionally, the capture step is then followed by at least two other intermediate purification or polishing chromatography steps to ensure adequate purity and viral clearance. The intermediate purification or polishing step is typically accomplished via affinity chromatography, ion exchange chromatography, or hydrophobic interaction, among other methods. In a traditional process, the final polishing step may be accomplished via ion exchange chromatography, hydrophobic interaction chromatography, or gel filtration chromatography. These steps remove process- and product-related impurities, including host cell proteins (HCP), DNA, leached protein A, aggregates, fragments, viruses, and other small molecule impurities from the product stream and cell culture.

FIG. 10 schematically shows an example of a purification process for purifying a monoclonal antibody from a cell culture harvest involving multiple process operations in order to meet purity, yield, and throughput requirements of the target substance. In this example, the sample containing the protein may first be clarified using any method known in the art (see FIG. 10, step 1). The clarification step seeks to remove cells, cell debris, and some host cell impurities from the sample. In an embodiment, the sample may be clarified via one or more centrifugation steps or via one or more depth filtration steps or via a microfiltration or ultrafiltration membrane in tangential flow filtration (TFF) mode.

In this example, following the clarification step of the invention, the sample may be subjected to a chromatography capture step (see FIG. 10, step 2). The capture step is designed to separate the target protein from other impurities present in the clarified sample. Often, the capture step reduces host cell protein (HCP), host cell DNA, and endogenous virus or virus-like particles in the sample. The chromatography technique utilized in this embodiment may be any technique known in the art to be used as a capture step. The sample may be subjected to affinity chromatography, ion exchange chromatography, mixed-mode chromatography, or hydrophobic interaction chromatography as a capture step. In particular, affinity chromatography may be utilized as the capture step. Affinity chromatography makes use of specific binding interactions between molecules. A particular ligand is chemically immobilized or "coupled" to a solid support. When the sample is passed over the resin, the protein in the sample, which has a specific binding affinity to the ligand, becomes bound. After other sample components are washed away, the bound protein is then stripped from the immobilized ligand and eluted, resulting in its purification from the original sample. The affinity chromatography capture step may comprise interactions between an antigen and an antibody, an enzyme and a substrate, or a receptor and a ligand. In a particular embodiment of the invention, the affinity chromatography capture step may comprise protein A chromatography, protein G chromatography, protein NG chromatography, or protein L chromatography.

Following the chromatography capture step, the eluate may be subjected to a combination processing step. This combination step may, in an embodiment, comprise viral inactivation followed by processing through one or more depth filers and ion-exchange membranes (see FIG. 10, step 3). In an embodiment, the depth filtration and ion-exchange membrane may be designed as a filter train, in series.

In this example, the viral inactivation step may comprise low-pH viral inactivation. In one aspect, use of a high concentration glycine buffer at low pH for elution may be employed, without further pH adjustment, in a final eluate pool in the targeted range for low-pH viral inactivation. Alternatively, the viral inactivation aspect of the combination processing step may be carried out using other methods known in the art. For example, the viral inactivation step may comprise, in various embodiments, treatment with acid, detergent, solvent, chemicals, nucleic acid cross-linking agents, ultraviolet light, gamma radiation, heat, or any other process known in the art to be useful for this purpose.

Following viral inactivation and neutralization, the inactivated eluate pool may be processed through one or more depth filters, and one or more ion-exchange membranes, hydrophobic membranes, or mixed-mode membranes, provided as a filter train or in series.

Following the combination processing step, the sample may be subjected to an intermediate/final polishing step (FIG. 10, step 4). This step may, in an embodiment, comprise an additional chromatography step. Any form of chromatography known in the art may be acceptable. For example, in an embodiment, the intermediate/final polishing step may comprise a mixed-mode (also known as multimodal) chromatography step. Alternatively or in combination, the intermediate/final polishing step may comprise a cation exchange chromatography (FIG. 10, step 4). The cation exchange chromatography step utilized in this invention may use any cation exchange chromatography process known in the art.

Alternatively or in combination, the intermediate/final polishing step may be accomplished via one or more membrane adsorbers or monoliths. Membrane adsorbers are thin, synthetic, microporous or macroporous membranes that are derivatized with functional groups akin to those on the equivalent resins. On their surfaces, membrane adsorbers carry functional groups, ligands, interwoven fibers, or reactants capable of interacting with at least one substance in contact within a fluid phase moving through the membrane by gravity.

Yet alternatively, the intermediate/final polishing step may be accomplished via an additional depth filtration step rather than by using membrane adsorbers, monoliths, or a mixed-mode column.

Following the intermediate/final polishing chromatography step, the eluate pool may be subjected to a nanofiltration step (see FIG. 10, step 5). In an embodiment, the nanofiltration step is accomplished via one or more nanofilters or viral filters.

As shown in FIG. 10, step 6, the nanofiltration step may be optionally followed by ultrafiltration/diafiltration (UF/DF), to achieve the targeted drug substance concentration and buffer condition before bottling. Alternatively, this can be accomplished by the use of filters. The nanofiltration and UF/DF steps can be combined or replaced by any process(es) known in the art known to provide a purified protein that is acceptable for bottling (FIG. 10, step 7).

FIG. 1 shows a schematic representation of a bioprocessing system 100 according to one or more embodiments of the present disclosure. The bioprocessing system 100 is configured to provide a desired system functionality, typically to receive input substances $S_{input\_1}$, $S_{input\_2}$, $S_{input\_3}$ and produce a desired target substance $S_{Desired}$.

In one example, the bioprocessing system 100 comprises a chromatography system configured to separate a desired target substance or sample $S_{Desired}$ from one or more input substances $S_{Input1}$-$S_{InputN}$, e.g. different mixtures of the sample and a buffer compositions.

Figure 2:
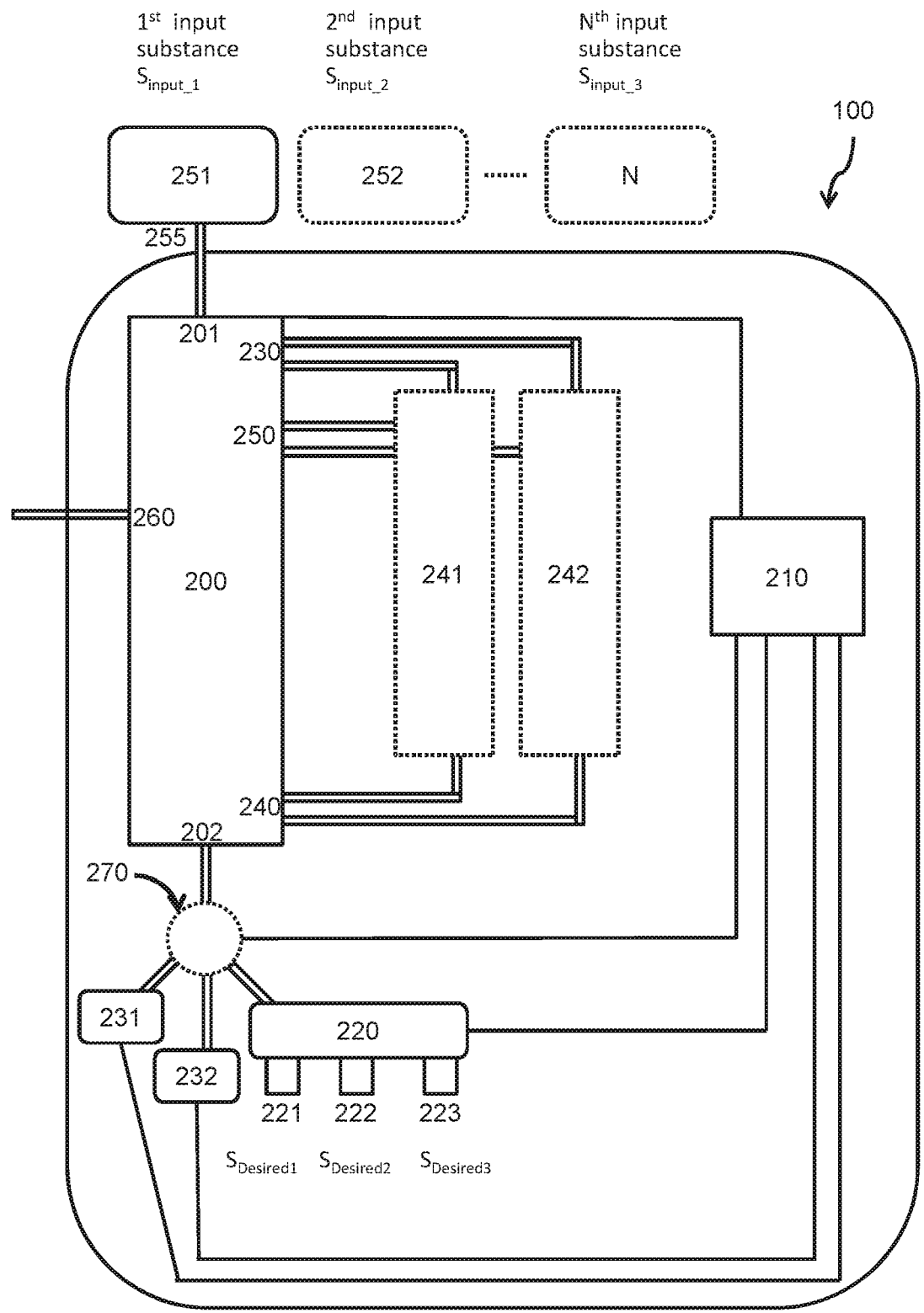
FIG. 2 shows an example of a bioprocessing system embodied as a chromatography bioprocessing system according to one or more embodiments of the disclosure.

FIG. 2 shows an example of a bioprocessing system 100 embodied as a chromatography bioprocessing system according to one or more embodiments of the disclosure. The bioprocessing system 100 may comprise a selection of bioprocessing units, such as a reservoir 251, a valve unit 200, a column 241, a splitter 270, a pH sensor 231, a conductivity sensor 232 and an outlet valve 220. The bioprocessing system 100 in the form of a chromatography bioprocessing system 100 is described in further detail below.

The chromatography bioprocessing system 100 may typically comprise at least one inlet 255. The inlet may optionally be coupled to one reservoirs 251 configured to hold a fluid. It is understood that the chromatography bioprocessing system 100 may comprise any number of reservoirs and inlets. The inlet 255 may e.g. be implemented as tubular elements such as a tube or hose. The chromatography bioprocessing system 100 may further comprise a valve unit 200. The valve unit 200 may be coupled to the reservoir 251 by the inlet 255 coupled to the fluid inlet 201. The valve unit 200 may be configured to be coupled to a first column 241 by a first pair of fluid ports 230 and/or configured to be coupled to a second column 242 by a second pair of fluid ports 240. The first column 241 and/or the second column 242 may be comprised in the chromatography bioprocessing system 100 or arranged external to the chromatography bioprocessing system 100. The chromatography bioprocessing system 100 may further comprise a control unit 210 which comprises circuitry, e.g. a processor and a memory. The memory may contain instructions executable by the processor, whereby said chromatography bioprocessing system is operative to perform any of the steps or methods described herein.

The chromatography bioprocessing system 100 may optionally comprise a splitter 270 coupled to the fluid outlet 202 of the valve unit 200 and coupled to a selection of any of a pH sensor 231, a conductivity sensor 232 and an outlet valve 220. The splitter 270 may be configured to direct fluid received from the injection unit 280 to any of any of the pH sensor 231, the conductivity sensor 232 and the outlet valve 220. Optionally the splitter 270 may be communicatively coupled to the control unit and perform coupling of fluid in in response to a control signal from the control unit 210.

The pH sensor 231 may be communicatively coupled to the control unit 210 and configured for measuring the pH of the fluid provided by the splitter 270. The chromatography bioprocessing system 100 may further comprise a conductivity sensor 232 communicatively coupled to the control unit 210 and configured for measuring the conductivity of the fluid provided by the splitter 270. The pH sensor 231 and/or the conductivity sensor 232 may further be configured to provide the measured pH and measured conductivity as control signals comprising measurement data to the control unit 210.

The chromatography bioprocessing system 100 may further comprise an outlet valve 220 coupled to the splitter 270.

The outlet valve 220 may have one or more outlets or outlet ports 221-223 and is configured to provide the fluid provided by the splitter 270 to the one or more outlets 221-223 in response to a control signal, e.g. received from the control unit 210.

Figure 3:
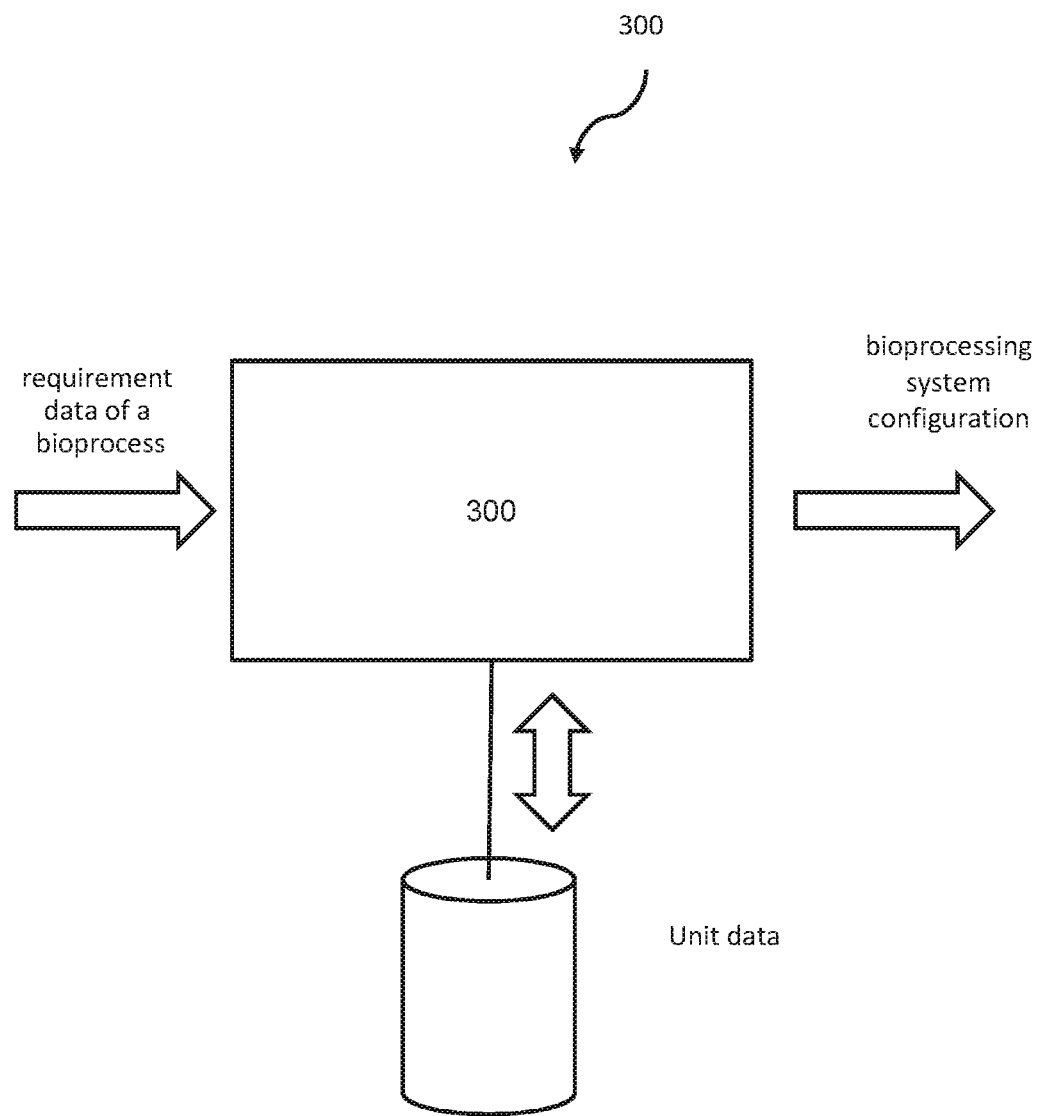
FIG. 3 illustrates flow of data to/from a computer performing a method according to one or more embodiments of the present disclosure.

FIG. 3 illustrates flow of data to/from a computer 300 (also referred to as configurator tool) performing a method 600 according to one or more embodiments of the present disclosure. The computer is further described in relation to FIG. 7. The computer 300 is configured for optimization of a bioprocessing system 100 formed by interconnected or interconnectable bioprocessing units and configured to provide a desired system functionality.

The computer is further configured to obtain requirement data of a bioprocess. The requirement data may be indicative of the desired bioprocessing system functionality. The requirement data may further be indicative of a desired substance $S_{Desired}$ resulting from the operation of the bioprocess system. The requirement data may be obtained by retrieving the requirement data as records from a memory, data storage device or database. The requirement data may optionally or additionally be obtained by compiling or calculating the requirement data. The compiled or calculated requirement data may further be stored as records to a memory, data storage device or database. The requirement data may optionally or additionally be obtained by receiving a user input signal indicative of user input or indications e.g. in response to end customer specific input regarding their product, process and process units and the like.

The requirement data may be indicative of e.g. dynamic binding capacity for chromatography resins, expected yield for a given process operation, dimensioning of process equipment for a given output, outcome from a given process scale, output or scale of the process or expected titer (concentration of target molecule) in a production bioreactor. However the requirement data is not limited thereto and may comprise any relevant requirement data related to the bioprocessing system or properties of the bioprocessing system.

The requirement data may further be indicative of a selection of any of a desired production scale, a desired amount of the desired substance, a desired output of the bioprocessing system, a physical area available for housing the system, a desired system running hours, a desired system service life or template system configurations. The template system configurations may further be indicative of an amounts and types of bioprocessing units comprised in the system and/or information on how the bioprocessing units are interconnected or interconnectable to each other. The requirement data may further be indicative of nominal price, nominal power consumption etc.

The computer is further configured to obtain unit data indicative of characteristics of a plurality of bioprocessing units, e.g. units disclosed in FIG. 11. The unit data may be obtained by retrieving the requirement data as records from a memory, data storage device or database. The unit data may optionally or additionally be obtained by compiling or calculating the unit data. The compiled or calculated unit data may further be stored as records to a memory, data storage device or database. The unit data may optionally or additionally be obtained by receiving a user input signal indicative of user input or indications.

The unit data may be indicative of a selection of any of specification data relating to each bioprocessing unit and/or characteristics relating to each bioprocessing unit of the plurality of bioprocessing units and/or or template bioprocessing system configurations. Examples of unit data include output or input capacity of unit; physical size; information if the unit is configured for single-use or reusable, a desired production scale, a desired amount of the desired substance, footprint of the unit, running hours of the unit or service life of the unit. The template bioprocessing system configurations may further be indicative of an amounts and types of bioprocessing units comprised in a template system and/or information on how the comprised bioprocessing units are interconnected or interconnectable to each other in the template system. The unit data may further be indicative of the units nominal price, nominal power consumption etc.

The unit data may further be indicative of e.g. dynamic binding capacity for chromatography resins, expected yield for a given process operation, dimensioning of process equipment for a given output, outcome from a given process scale, output or scale of the process or expected titer (concentration of target molecule) in a production bioreactor. However the unit data is not limited thereto and may comprise any relevant unit data related to the bioprocessing units or properties of the bioprocessing units.

The computer is further configured to generate at least one optimized or suitable bioprocessing system configuration, capable to provide the desired system functionality, using the requirement data, the unit data and an objective function dependent on the requirement data and the unit data. The computer may further be configured to generate at least one optimized or suitable bioprocessing system configuration based on or using the template system configurations or existing system configurations indicated by a user. The template system configurations may be comprised in the requirement data and/or the unit data. Alternatively or additionally the template system configurations may be indicated as existing system configurations, e.g. indicated by a user.

The at least one optimized or suitable bioprocessing system configuration is generated by performing a selection of bioprocessing units from the plurality of bioprocessing units, where the bioprocessing units are selected using the requirement data the unit data and an objective function dependent on the requirement data and the unit data.

In an embodiment, the computer is configured to generate the at least one optimized or suitable bioprocessing system configuration by identifying one or more candidate system configurations using the requirement data and the unit data, wherein a system configuration is identified if the unit data match the requirement data and selecting the at least one optimized or suitable bioprocessing system configuration by optimizing a value of an objective function dependent on the requirement data and the unit data.

In one example, the requirement data is indicative of the desired bioprocessing system functionality to produce the desired substance $S_{Desired}$ at a particular volume per hour. The objective function is dependent on substance and volume per hour. The computer will then evaluate the objective function on all bioprocessing units, arranged according to the template system configurations or existing system configurations indicated by a user, capable to produce the desired substance $S_{Desired}$ at the particular volume per hour. One optimized or suitable bioprocessing system configuration is then generated comprising a selection of bioprocessing units that optimizes, i.e. minimizes or maximizes, the objective function.

In an embodiment, the computer is configured to select a plurality of optimized or suitable bioprocessing system configuration by optimizing a plurality of values of the objective function dependent on the requirement data and ranking the selected plurality of optimized or suitable bioprocessing system configurations using the plurality of values of the objective function.

In one example, the requirement data is indicative of the desired system functionality to produce the desired substance $S_{Desired}$ at a particular volume per hour. The objective function is dependent on substance and volume per hour. The computer will then evaluate the objective function on all bioprocessing units, arranged according to the template system configurations or existing system configurations indicated by a user, capable to produce the desired substance $S_{Desired}$ at the particular volume per hour. A plurality of optimized or suitable bioprocessing system configurations are then generated, each comprising a selection of bioprocessing units that optimizes, i.e. minimizes or maximizes, the objective function. The plurality of optimized or suitable bioprocessing system configurations are then ranked in an ascending or descending order using the corresponding value of the objective function.

Figure 4A:
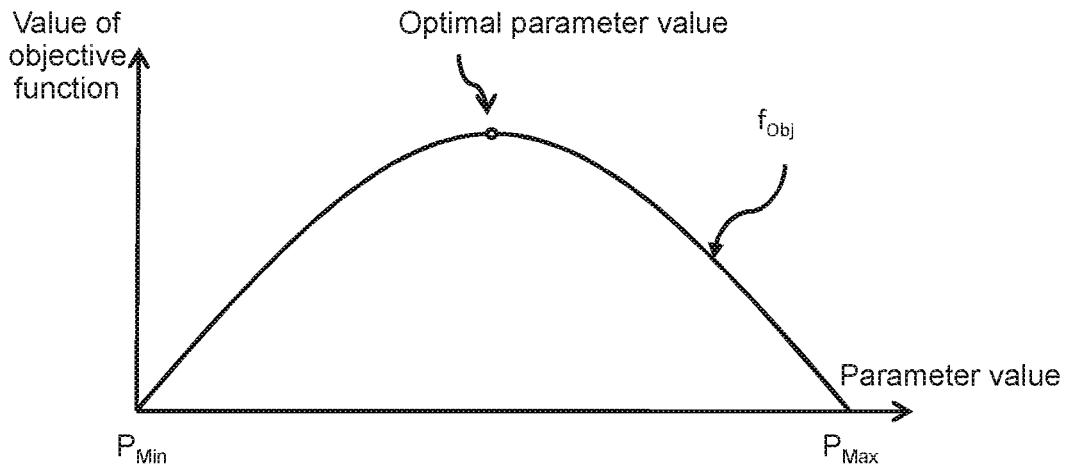
FIG. 4A illustrates an objective function according to one or more embodiments of the present disclosure.

FIG. 4A illustrates an objective function $f_{Obj}$ according to one or more embodiments of the present disclosure. The objective function is dependent on a parameter value and will generate a value of the objective function $f_{Obj}$ dependent on the parameter value. The objective function $f_{Obj}$ is evaluated over a parameter range $P_{Min}$-$P_{Max}$, which is defined by the characteristics of the bioprocessing units comprised in the unit data.

The objective function $f_{Obj}$ is configured to generate a maximal value at an optimal/optimized parameter value. It is understood that the objective function $f_{Obj}$ may be dependent on any number of parameters, thus implementing multidimensional optimization, as further described in relation to FIG. 5.

Figure 4B:
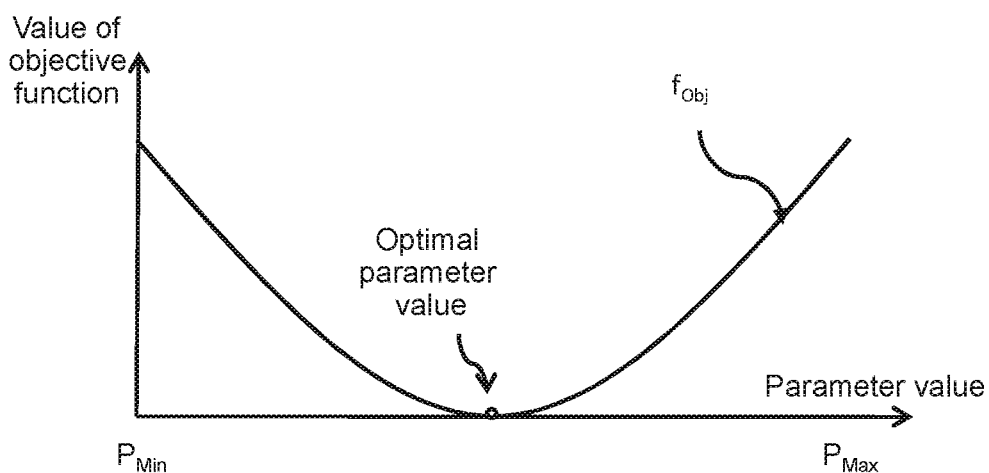
FIG. 4B illustrates an objective function according to one or more embodiments of the present disclosure.

FIG. 4B illustrates an objective function $f_{Obj}$ according to one or more embodiments of the present disclosure. The objective function is dependent on a parameter value and will generate a value of the objective function $f_{Obj}$ dependent on the parameter value. The objective function $f_{Obj}$ is evaluated over a parameter range $P_{Min}$-$P_{Max}$, which is defined by the characteristics of the bioprocessing units comprised in the unit data.

The objective function $f_{Obj}$ is configured to generate a minimal value at an optimal/optimized parameter value. It is understood that the objective function $f_{Obj}$ may be dependent on any number of parameters, thus implementing multidimensional optimization, as further described in relation to FIG. 5.

In one example, the requirement data indicate that a template system configuration, according to the system configuration shown in FIG. 2, requires a column 241 providing a volume of X liters. The method will then identifying all candidate columns comprised in the unit data that can provide a volume of X liters.

An objective function generating a value of the objective function $f_{Obj}$ may be defined as:

$$f_{Obj} = |V_{Candidate} - X|, \text{ where } V_{Candidate} \text{ is the volume of a candidate column}$$

One optimized or suitable bioprocessing system configuration in the form of a column is then selected by optimizing the value of the objective function $f_{Obj}$ dependent on the requirement data X and the unit data $V_{Candidate}$. In other words, the column with a volume closest to the desired volume is then selected as the optimized or suitable bioprocessing system configuration.

Figure 5:
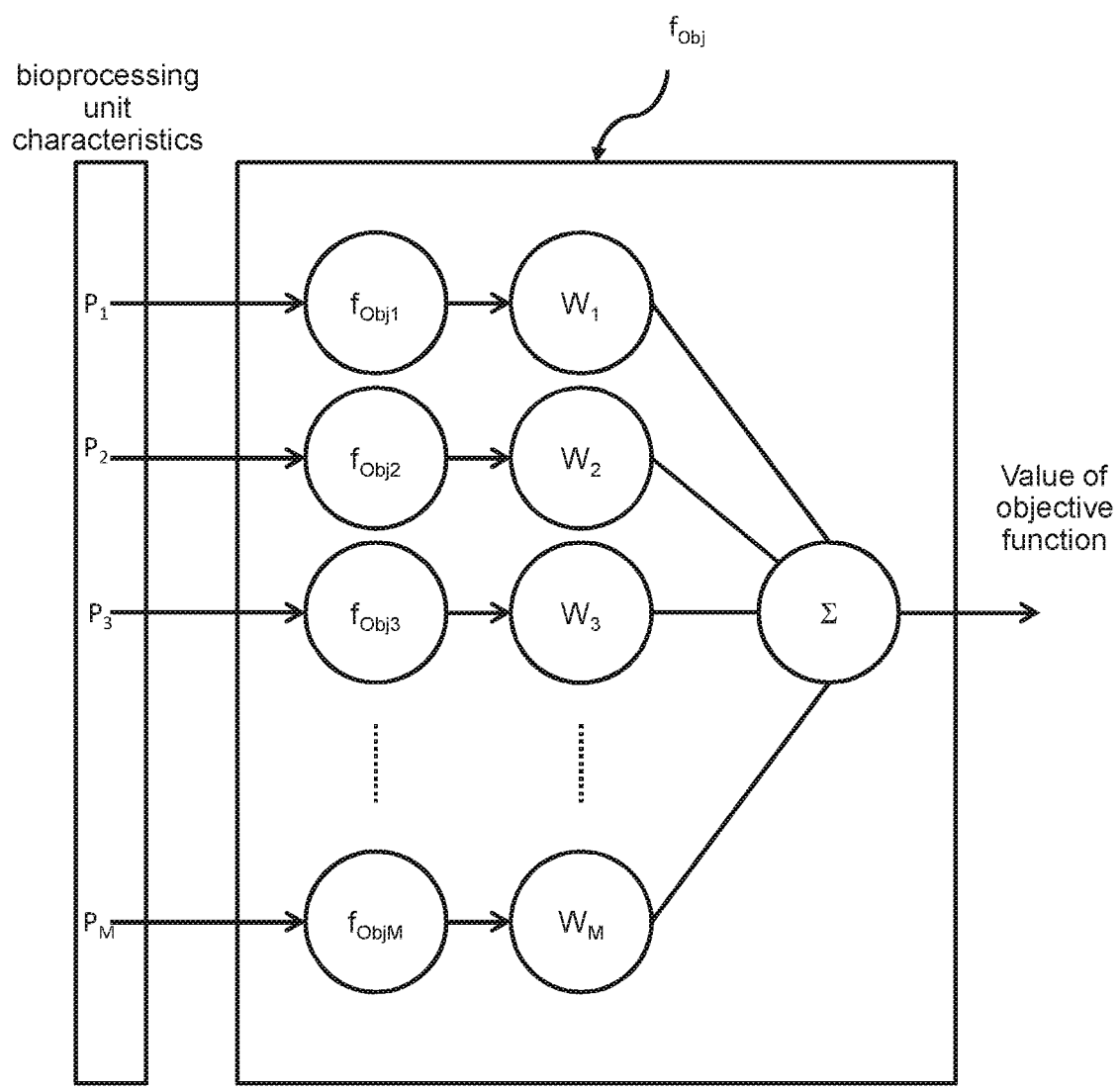
FIG. 5 illustrates a multidimensional objective function according to one or more embodiments of the present disclosure.

FIG. 5 illustrates a multidimensional objective function $f_{Obj}$ according to one or more embodiments of the present disclosure. In one embodiment, the objective function $f_{Obj}$ is dependent on a plurality of parameters $P_1$-$P_M$ and corresponding values. The objective function $f_{Obj}$ will generate a value of the objective function dependent on the parameter values. The objective function $f_{Obj}$ will generate a maximal value or minimal value at an optimal/optimized parameter value.

Each bioprocessing unit of the plurality of bioprocessing units will have characteristics comprising the plurality of parameter $P_1$-$P_M$ values, associated to the bioprocessing unit/s comprised in the unit data.

Each parameter value of the plurality of parameter $P_1$-$P_M$ values will be processed using a corresponding parameter objective function $f_{Obj1}$-$f_{ObjM}$, further described in relation to FIG. 4A-4B.

The degree or part of to which extent that each parameter objective function $f_{Obj1}$-$f_{ObjM}$ will influence the value of the objective function is determined with a corresponding weight $W_1$-$W_M$ multiplied with the corresponding parameter objective function $f_{Obj1}$-$f_{ObjM}$.

In one example, the requirement data indicate that a template system configuration, according to the system configuration shown in FIG. 2, requires a column 241 providing a volume of X liters and having a porosity of 10 µm. The method will then identifying all candidate columns comprised in the unit data that can provide a volume of X liters and has a porosity Y of 10 µm.

An objective function generating a value of the objective function $f_{Obj}$ may be defined as:

$$f_{Obj} = |V_{Candidate} - X| +,$$

$$f\text{Obj} = |V_{Candidate} - X| * W_1 + |POROSITY_{Candidate} - Y| * W_2$$

where $V_{Candidate}$ is the volume of a candidate column and $POROSITY_{Candidate}$ is the porosity of the same candidate column.

One optimized or suitable bioprocessing system configuration in the form of a column is then selected by optimizing the value of the objective function $f_{Obj}$ dependent on the requirement data comprising X and Y, the unit data comprising $V_{Candidate}$, and the $POROSITY_{Candidate}$. In other words, the column with a volume and porosity closest to the desired volume and desired porosity, is then selected as the optimized or suitable bioprocessing system configuration.

It is understood that this teaching can be extended to any number of parameters.

Figure 6:
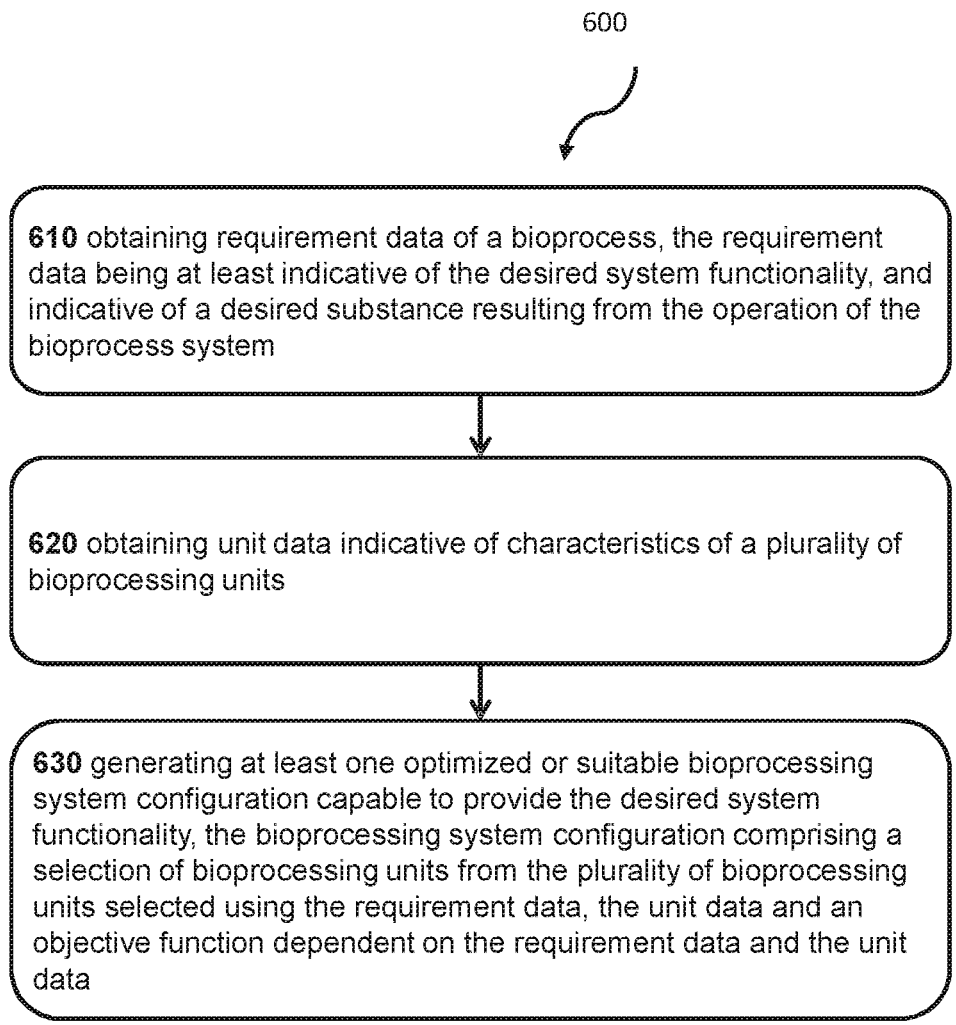
FIG. 6 shows a flowchart of a method according to one or more embodiments of the present disclosure.

FIG. 6 shows a flowchart of a method according to one or more embodiments of the present disclosure. A computer implemented method 600 for optimization of a bioprocessing system 100 formed by interconnected or interconnectable bioprocessing units is provided and configured to provide a desired system functionality. The method comprising:

Step 610: obtaining requirement data of a bioprocess, the requirement data being at least indicative of the desired system functionality, and indicative of a desired substance resulting from the operation of the bioprocessing system.

Obtaining requirement data is further described in relation to FIG. 3 and may e.g. be performed by receiving indications from a user.

Step 620: obtaining unit data indicative of characteristics of a plurality of bioprocessing units.

Obtaining unit data further described in relation to FIG. 3 and may e.g. be performed by retrieving bioprocessing unit characteristics comprised in records from a database.

Step 630: generating at least one optimized or suitable bioprocessing system configuration capable to provide the desired system functionality. The generated bioprocessing system configuration comprises a selection of bioprocessing units from the plurality of bioprocessing units selected using the requirement data, the unit data and an objective function dependent on the requirement data and the unit data.

In one embodiment, the at least one optimized or suitable bioprocessing system configuration is generated based on or using template system configurations indicative of type of bioprocessing units comprised in the system and information on how the bioprocessing units are interconnected or interconnectable to each other.

In embodiments, the template system configurations may be comprised in the unit data and/or the requirement data and/or may be indicated as existing system configurations or existing partial system configurations, e.g. indicated by a user.

In one embodiment, the template system configurations may be obtained by retrieving the template system configurations as records from a memory, data storage device or database. The template system configurations may optionally or additionally be obtained by compiling or calculating the template system configurations. The compiled or calculated template system configurations may further be stored as records to a memory, data storage device or database. The template system configurations may optionally or additionally be obtained by receiving a user input signal indicative of user input or indications.

In one embodiment, the step of generating bioprocessing system configurations comprises:

identifying one or more candidate system configurations using the requirement data and the unit data, wherein a system configuration is identified if the unit data match the requirement data, selecting the at least one optimized or suitable bioprocessing system configuration by optimizing a value of an objective function dependent on the requirement data and the unit data.

Optimizing a value of an objective function is further described in relation to FIG. 4A, 4B and FIG. 5.

In one embodiment, a plurality of optimized or suitable bioprocessing system configuration are selected by optimizing a plurality of values of the objective function dependent on the requirement data and ranking the selected bioprocessing system configurations using the plurality of values of the objective function.

In one embodiment, obtaining unit data comprises compiling or reading records in a database, accessible by the computer, the unit data including specification data or characteristics relating to each bioprocessing unit.

In one embodiment, obtaining requirement data comprises receiving input of requirement data from a user.

In one embodiment, the requirement data is indicative of a selection of any of a desired production scale, a desired amount of the desired substance, a desired output of the system, a physical area available for housing the system, a desired system running hours, a desired system service life, unit cost/price or template system configurations. The template system configurations being indicative of type of bioprocessing units comprised in the system and information on how the bioprocessing units are interconnected or interconnectable to each other.

In one embodiment, the unit data is indicative of a selection of any of output or input capacity of unit; physical size; information if the unit is configured for single-use or reusable, a desired production scale, a desired amount of the desired substance, footprint of the unit, running hours of the unit or service life of the unit, unit cost/price or template system configurations. The template system configurations being indicative of type of bioprocessing units comprised in the system and information on how the bioprocessing units are interconnected or interconnectable to each other.

In one embodiment, the configurator tool 300 may be used to provide an optimized process configuration for production of a desired amount of target substance in a defined time frame. In addition, the requirement data may comprise further limitation such as working hours at the production facilities e.g. 8 hours per day with no night shifts, whereby the configuration tool is arranged to optimize the process configuration such that no sequence of process operations that cannot be put on hold over night, and which sequence need operator interaction or the like is longer than 8 hours. In one example the purification and viral clearance core process step may be such a rate limiting process, whereby the optimization would result in provision of a process configuration allowing higher throughput in this step. In one embodiment, the configurator tool 300 is arranged to provide estimations of utility supply for the optimized process configuration, as well as volumes of waste liquid from the process for verification that supply chain for incoming supplies and outgoing waste is sufficient.

In one embodiment as indicated below with reference to FIG. 8, the configurator tool 300 is arranged to retrieve information regarding availability etc. of process units and based on such data provide information regarding the effect of specific selections of process units, e.g. delivery time, service intervals etc.

In one embodiment, the optimized or suitable bioprocessing system configuration comprises at least information indicative of the identity of the selection of bioprocessing units.

In one embodiment, the optimized or suitable bioprocessing system configuration further comprises information indicative of on how the selection of bioprocessing units are interconnected or interconnectable to each other.

In one embodiment, a computer is provided, wherein the computer is configured to perform any of the method steps of the method described herein.

In one embodiment, a computer program is provided comprising computer-executable instructions for causing a computer, when the computer-executable instructions are executed on a processing unit comprised in the computer, to perform any of the method steps of the method described herein.

In one embodiment, a computer program product is provided comprising a computer-readable storage medium, the computer-readable storage medium having the computer program above embodied therein.

In one embodiment, a carrier containing the computer program above is provided, wherein the carrier is one of an electronic signal, optical signal, radio signal, or computer readable storage medium.

Figure 7:
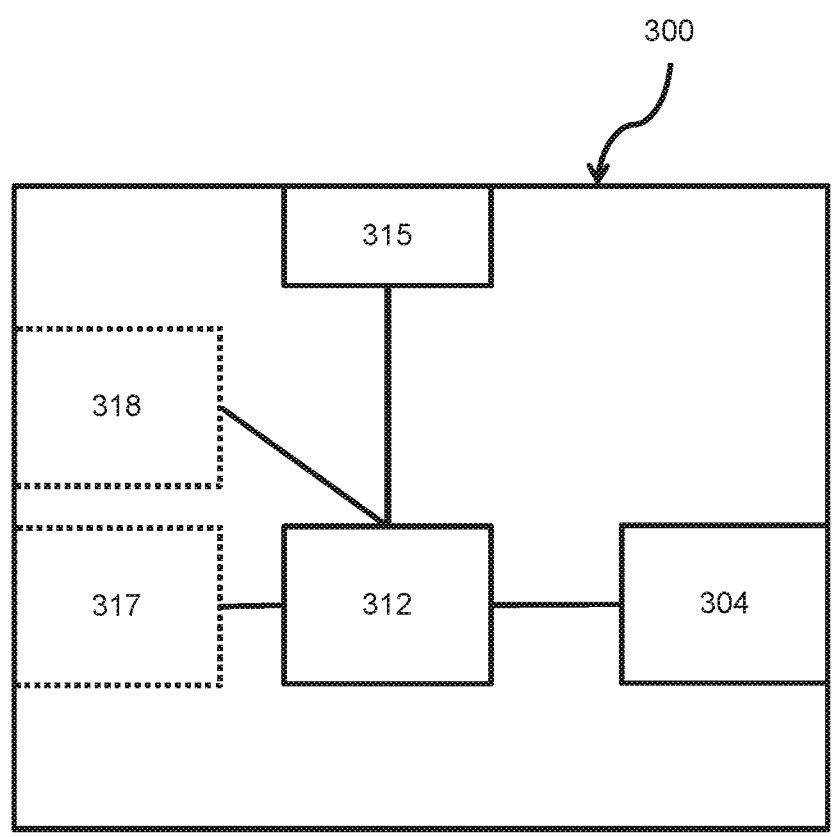
FIG. 7 shows the computer 300 according to one or more embodiments of the present disclosure.

FIG. 7 shows the computer 300 according to one or more embodiments of the present disclosure. The computer 300 may be in the form of e.g. an Electronic Computer, a server, an on-board computer, a stationary computing device, a laptop computer, a tablet computer, a handheld computer, a wrist-worn computer, a smart watch, a smartphone or a smart TV. The computer 300 may comprise processing circuitry 312 communicatively coupled to a transceiver 304 configured for wired or wireless communication. The computer 300 may further comprise at least one optional antenna (not shown in figure). The antenna may be coupled to the transceiver 304 and is configured to transmit and/or emit and/or receive wired or wireless signals in a communication network, such as WiFi, Bluetooth, 3G, 4G, 5G etc. In one example, the processing circuitry 312 may be any of a selection of a processor and/or a central processing unit and/or processor modules and/or multiple processors configured to cooperate with each-other. Further, the computer 300 may further comprise a memory 315. The memory 315 may e.g. comprise a selection of a hard RAM, disk drive, a floppy disk drive, a flash drive or other removable or fixed media drive or any other suitable memory known in the art. The memory 315 may contain instructions executable by the processing circuitry to perform any of the steps or methods described herein. The processing circuitry 312 may be communicatively coupled to a selection of any of the transceiver 304 and the memory 315. The computer 300 may be configured to send/receive control signals directly to any of the above mentioned units or to external nodes or to send/receive control signals via a wired and/or wireless communications network.

The wired/wireless transceiver 304 and/or a wired/wireless communications network adapter may be configured to send and/or receive data values or parameters as a signal to or from the processing circuitry 312 to or from other external nodes.

In an embodiment, the transceiver 304 communicates directly to external nodes or via the wireless communications network.

In one or more embodiments the computer 300 may further comprise an input device 317, configured to receive input or indications from a user and send a user input signal indicative of the user input or indications to the processing circuitry 312.

In one or more embodiments the computer 300 may further comprise a display 318 configured to receive a display signal indicative of rendered objects, such as text or graphical user input objects, from the processing circuitry 312 and to display the received signal as objects, such as text or graphical user input objects.

In one embodiment the display 318 is integrated with the user input device 317 and is configured to receive a display signal indicative of rendered objects, such as text or graphical user input objects, from the processing circuitry 312 and to display the received signal as objects, such as text or graphical user input objects, and/or configured to receive input or indications from a user and send a user-input signal indicative of the user input or indications to the processing circuitry 312.

In a further embodiment, the computer 300 may further comprise and/or be coupled to one or more additional sensors (not shown in the figure) configured to receive and/or obtain and/or measure physical properties pertaining to the bioprocessing system and send one or more sensor signals indicative of the physical properties to the processing circuitry 312.

In one or more embodiments, the processing circuitry 312 is further communicatively coupled to the input device 317 and/or the display 318 and/or the additional sensors.

In embodiments, the communications network communicates using wired or wireless communication techniques that may include at least one of a Local Area Network (LAN), Metropolitan Area Network (MAN), Global System for Mobile Network (GSM), Enhanced Data GSM Environment (EDGE), Universal Mobile Telecommunications System, Long term evolution, High Speed Downlink Packet Access (HSDPA), Wideband Code Division Multiple Access (W-CDMA), Code Division Multiple Access (CDMA), Time Division Multiple Access (TDMA), Bluetooth®, Zigbee®, Wi-Fi, Voice over Internet Protocol (VoIP), LTE Advanced, IEEE802.16m, WirelessMAN-Advanced, Evolved High-Speed Packet Access (HSPA+), 3GPP Long Term Evolution (LTE), Mobile WiMAX (IEEE 802.16e), Ultra Mobile Broadband (UMB) (formerly Evolution-Data Optimized (EV-DO) Rev. C), Fast Low-latency Access with Seamless Handoff Orthogonal Frequency Division Multiplexing (Flash-OFDM), High Capacity Spatial Division Multiple Access (iBurst®) and Mobile Broadband Wireless Access (MBWA) (IEEE 802.20) systems, High Performance Radio Metropolitan Area Network (HIPERMAN), Beam-Division Multiple Access (BDMA), World Interoperability for Microwave Access (Wi-MAX) and ultrasonic communication, etc., but is not limited thereto.

Moreover, it is realized by the skilled person that the computer 300 may comprise the necessary communication capabilities in the form of e.g., functions, means, units, elements, etc., for performing the present solution. Examples of other such means, units, elements and functions are: processors, memory, buffers, control logic, encoders, decoders, rate matchers, de-rate matchers, mapping units, multipliers, decision units, selecting units, switches, interleavers, de-interleavers, modulators, demodulators, inputs, outputs, antennas, amplifiers, receiver units, transmitter units, DSPs, MSDs, TCM encoder, TCM decoder, power supply units, power feeders, communication interfaces, communication protocols, etc. which are suitably arranged together for performing the present solution.

Especially, the processing circuitry of the present disclosure may comprise one or more instances of a processor, processor modules and multiple processors configured to cooperate with each-other, Central Processing Unit (CPU), a processing unit, a processing circuit, a processor, an Application Specific Integrated Circuit (ASIC), a microprocessor, a Field-Programmable Gate Array (FPGA) or other processing logic that may interpret and execute instructions. The expression "processing circuitry" and/or "processing means" may thus represent a processing circuitry comprising a plurality of processing circuits, such as, e.g., any, some or all of the ones mentioned above. The processing means may further perform data processing functions for inputting, outputting, and processing of data comprising data buffering and device control functions, such as call processing control, user interface control, or the like.

Figure 8:
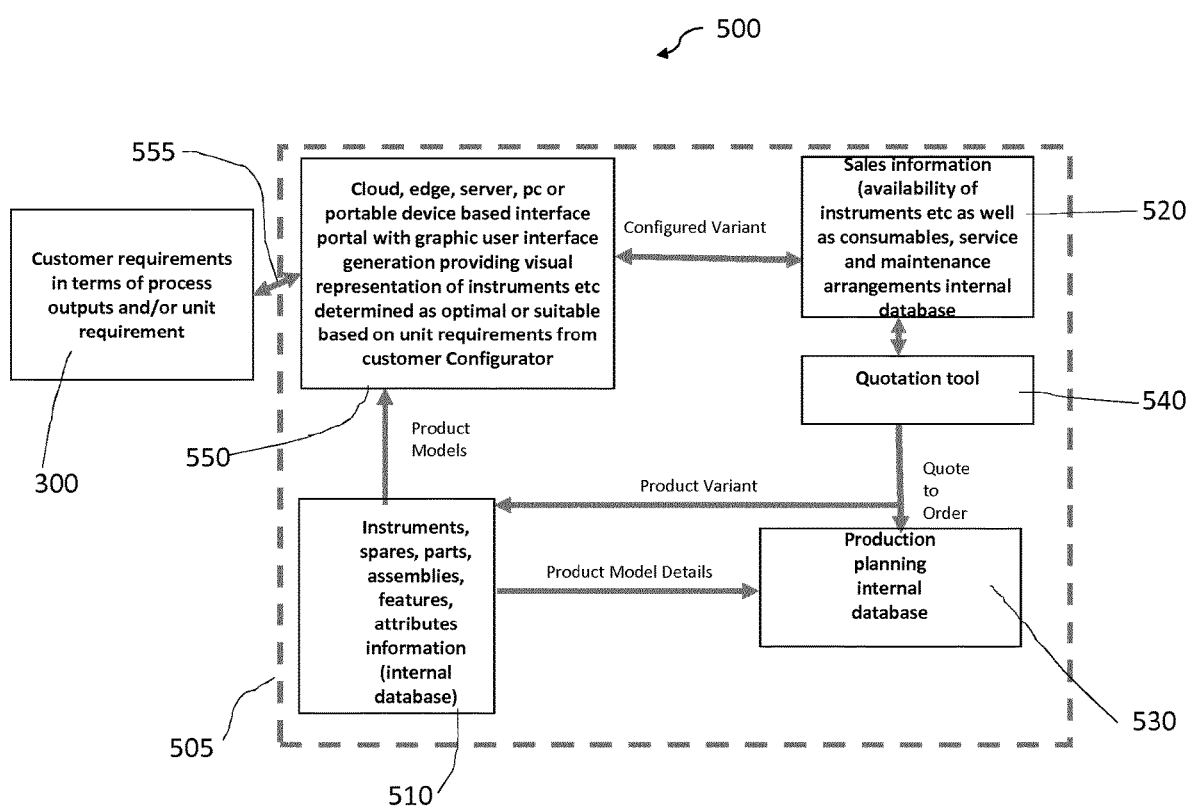
FIG. 8 shows a schematic representation of one embodiment of the disclosure showing a configuration system incorporating the computer 300.

FIG. 8 shows a schematic embodiment of a system layout of an extended configuration system 500 of the present invention wherein the the computer 300 performing a method 600 according to one or more embodiments of the present disclosure is arranged to interact with a configurator extension module 505 arranged to provide additional functionality to the overall configurator setup. The configurator extension module 505 may comprise an interface portal 550 with graphic user interface generation arranged to provide a visual representation of instruments etc determined as optimal or suitable system configuration based on unit requirements and other input from the configurator tool 300. Further, The extended configuration module 505 may comprise a bioprocessing unit database 510 which in turn may be linked to a production planning tool 530

According to one embodiment the computer 300 mentioned above forms part of the bioprocessing system for controlling that system, and can be used as a dedicated control means. However, in the embodiment shown in FIG. 8 the computer 300 is connected or connectable with a configuration system 500 shown in FIG. 8. FIG. 8 shows the above mentioned computer 300 connected to a configurator extension module 505 which may be embodied as an otherwise closed network, for use with the methods described above. The closed network includes an interface portal 550 which may be embodied as a configuration computer, which may have the same attributes as the bioprocessing system computer 300 which performs the configuration methods described above. The interface portal configuration computer 550 is in network communication with a further computer hosting a bioprocessing unit database 510, including data relating to unit parameters such as: rated inputs; rated outputs; cycle times; batch time; physical size, energy consumption etc. The computer 550 is also in network communication with a further computer, hosting a Sales information database 520, for providing data relating to unit availability, compatibility with other units, consumables required, consumable supply information, service and maintenance information, regulatory information and training information.

Linked in a network to the computers 510 and 520 are further systems 530 and 540 providing to both computers 510 and 520 data relating to unit and consumable availability, and financial information for providing a price quote to the customer.

In one embodiment the customer may have access to the configuration system 500 via a gateway 555, which could be a conventional internet access, which allows the customer limited access to the computer 550, for inputting the requirement data, as described above to the computer 550, from the controlling bioprocessing computer 300. It will be apparent that the access to the configuration system 500 could be made via any alternative suitably configured computer or device, and not necessarily a computer 300 that controls a bioprocessing system.

It should be understood that the above mentioned embodiment described in relation to FIG. 8 is just example of a configuration system, where data is held in a closed network for confidentiality reasons, and where methods for configuring a bioprocessing system are performed within the closed network. In a variant, it would be possible for the customer's computer 300 to store, or access directly the necessary data, and to perform the methods for configuration, although that is not preferred because data may then be extracted for the databases accessed.

Figure 9:
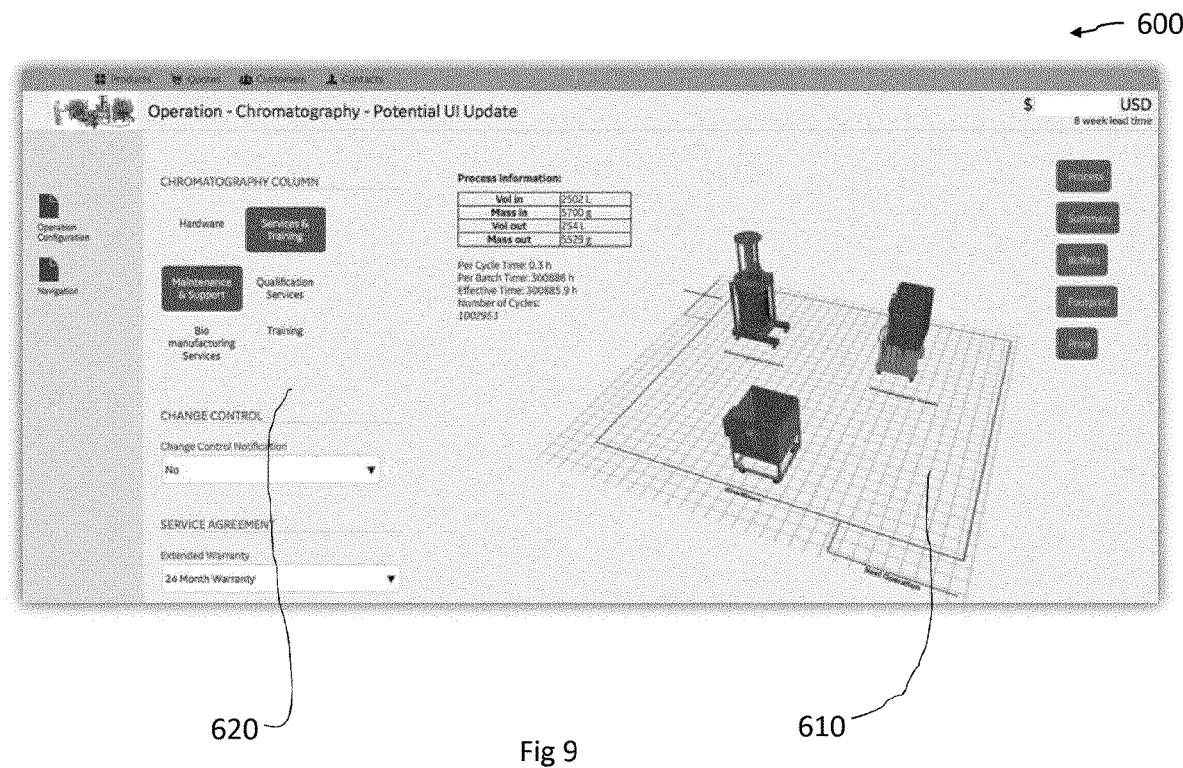
FIG. 9 shows a typical graphical user interface showing a spatial representation of bioprocessing units determined by the method disclosed herein and other determined parameters.

The bioprocess configuration can be presented in the form shown in FIG. 9, for display on a display of the computer 300 or the display of the alternative computer or device mentioned immediately above, wherein, a graphical user interface 600 includes, for example, identification of suitable bioprocessing units in a three dimensional spatial representation 610 together with other information 620 needed to confirm the suitability of the system units determined by the methods described above, as well as price.

Finally, it should be understood that the invention is not limited to the embodiments described above, but also relates to and incorporates all embodiments within the scope of the appended independent claims.

The invention claimed is:

1. A computer implemented method for optimization of a bioprocessing system formed by interconnected or interconnectable bioprocessing units and configured to provide a desired system functionality, the method comprising:
   obtaining requirement data of a bioprocess comprising producing or separating a desired substance of interest from a composition, the requirement data being at least indicative of the desired system functionality, and indicative of the desired substance resulting from the operation of the bioprocess system,
   obtaining unit data indicative of characteristics of a plurality of bioprocessing units, generating at least one optimized or suitable bioprocessing system configuration capable to provide the desired system functionality based at least in part on multidimensional optimization of a plurality of parameter objective functions of a global objective function, the bioprocessing system configuration comprising a selection of bioprocessing units from the plurality of bioprocessing units, wherein the selected bioprocessing units are selected using the requirement data, the unit data and the plurality of parameter objective functions dependent on the requirement data and the unit data, and controlling the bioprocessing system, based on the at least one optimized or suitable bioprocessing system configuration, to execute the bioprocess to produce or separate the desired substance of interest from the composition.

2. The method according to claim 1, wherein the step of generating bioprocessing system configurations comprises:
identifying one or more candidate system configurations using the requirement data and the unit data, wherein a system configuration is identified if the unit data match the requirement data,
selecting the at least one optimized or suitable bioprocessing system configuration by optimizing at least a first value of a first parameter objective function of the plurality of parameter objective functions, wherein determination of the first value is dependent on the requirement data and the unit data.

3. The method according to claim 2, wherein a plurality of optimized or suitable bioprocessing system configuration are selected by optimizing a plurality of values of the plurality of parameter objective functions dependent on the requirement data, and
ranking the selected bioprocessing system configurations using the plurality of values of the plurality of parameter objective functions.

4. The method according to claim 1, wherein obtaining unit data comprises compiling or reading records in a database, accessible by the computer, the unit data including specification data relating to each bioprocessing unit.

5. The method according to claim 1, wherein obtaining requirement data comprises receiving input of requirement data from a user.

6. The method according to claim 1, wherein the requirement data is indicative of a selection of any of a desired production scale, a desired amount of the desired substance, a desired output of the system, a physical area available for housing the system, a desired system running hours, a desired system service life or template system configurations indicative of type of bioprocessing units comprised in the system and information on how the bioprocessing units are interconnected or interconnectable to each other.

7. The method according to claim 1, wherein the unit data is indicative of a selection of any of output or input capacity of unit, physical size, information if the unit is configured for single- use or reusable, a desired production scale, a desired amount of the desired substance, footprint of the unit, running hours of the unit, service life of the unit or template system configurations indicative of type of bioprocessing units comprised in the system and information on how the bioprocessing units are interconnected or interconnectable to each other.

8. The method according to claim 1, wherein the optimized or suitable bioprocessing system configuration comprises at least information indicative of the identity of the selection of bioprocessing units.

9. The method according to claim 8, wherein the optimized or suitable bioprocessing system configuration further comprises information indicative of how the selection of bioprocessing units are interconnected or interconnectable to each other.

10. The method according to claim 1, wherein the plurality of parameter objective functions are configured to generate respective maximal or minimal values at an optimized bioprocessing system configuration.

11. A computer, wherein the computer is configured to perform the method according to claim 1.

12. A configuration system for performing the method of claim 1, the system including;
the computer;
a database including data relating at least to bioprocessing unit parameters comprising one or more of output or input capacity rated inputs, cycle times, batch time, physical size, energy consumption, configuration for single-use or reusability, or service life,
the database, or a further database including data relating to one or more of unit availability, compatibility with other units, consumables required, consumable supply information, service and maintenance information, regulatory information and training information;
the computer and the database(s) being in communication via a network, and wherein the requirement data provided via a user gateway and the gateway returns the optimized or suitable bioprocessing system configuration.

13. The configuration system as claimed in claim 12, wherein the computer provides, via the gateway, data to a user including any one or more of: a three dimensional spatial representation of the bioprocessing system configured according to the bioprocessing system configuration, unit availability, compatibility with other units, consumables required, consumable supply information, service and maintenance information, or regulatory information and training information.

14. A computer program comprising computer-executable instructions for causing a computer, when the computer-executable instructions are executed on a processing unit comprised in the computer, to perform any of the method steps according to claim 1.

15. A computer program product comprising a computer-readable storage medium, the computer-readable storage medium having the computer program according to claim 14 embodied therein.

* * * * *